(12) United States Patent
Noar

(10) Patent No.: US 9,138,291 B2
(45) Date of Patent: Sep. 22, 2015

(54) CATHETER STRUCTURE AND METHOD FOR LOCATING TISSUE IN A BODY ORGAN AND SIMULTANEOUSLY DELIVERING THERAPY AND EVALUATING THE THERAPY DELIVERED

(71) Applicant: Mark D. Noar, Owings Mills, MD (US)

(72) Inventor: Mark D. Noar, Owings Mills, MD (US)

( * ) Notice: Subject to any disclaimer, the term of this patent is extended or adjusted under 35 U.S.C. 154(b) by 0 days.

(21) Appl. No.: 14/267,967

(22) Filed: May 2, 2014

(65) Prior Publication Data

US 2014/0243814 A1 Aug. 28, 2014

Related U.S. Application Data

(62) Division of application No. 13/409,138, filed on Mar. 1, 2012, now Pat. No. 8,753,340.

(51) Int. Cl.
*A61B 18/18* (2006.01)
*A61B 18/04* (2006.01)
*A61F 2/00* (2006.01)
(Continued)

(52) U.S. Cl.
CPC ........... *A61B 18/1492* (2013.01); *A61B 5/0492* (2013.01); *A61B 5/04884* (2013.01); *A61B 5/6852* (2013.01); *A61B 18/02* (2013.01); *A61B 18/18* (2013.01); *A61B 18/24* (2013.01); *A61N 1/0507* (2013.01); *A61N 1/0509* (2013.01); *A61N 1/36007* (2013.01); *A61B 5/4238* (2013.01); *A61B 17/320068* (2013.01); *A61B 18/06* (2013.01); *A61B 18/08* (2013.01); *A61B 18/1815* (2013.01); *A61B 18/20* (2013.01); *A61B 2018/00494* (2013.01); *A61B 2018/00577* (2013.01); *A61B 2018/00839* (2013.01); *A61B 2018/0212* (2013.01); *A61B 2018/1861* (2013.01)

(58) Field of Classification Search
CPC ............... A61B 18/20; A61B 18/1492; A61B 2018/00494; A61B 5/6823; A61B 5/4238; A61N 1/36007
USPC ............. 606/14, 46–50, 34, 41; 607/101–102
See application file for complete search history.

(56) References Cited

U.S. PATENT DOCUMENTS 5,690,691 A 11/1997 Chen et al.
5,776,073 A 7/1998 Garfield et al.
(Continued)

OTHER PUBLICATIONS

PCT Search Report & Written Opinion in PCT/US2013/26008, dated Apr. 28, 2013.

*Primary Examiner* — Lynsey Crandall
*Assistant Examiner* — Sebastian X Lukjan
(74) *Attorney, Agent, or Firm* — Manelli Selter PLLC; Edward J. Stemberger

(57) ABSTRACT

A catheter structure is provided for use with an electroviscerogram (EVG) system. The catheter structure includes an elongated tube structure having distal and proximal ends. Three electrodes are associated with distal end of the tube structure and are constructed and arranged obtain signals relating to myoelectrical activity internally of an intra-abdominal organ to thereby locate targeted tissue that includes main pathways of electrical generation in the organ. Therapy delivery structure, associated with the distal end of the tube structure and separate from the electrodes, is constructed and arranged to provide therapy at the targeted tissue simultaneously as the electrodes obtain the signals at the targeted tissue so that effectiveness of the therapy can be monitored.

7 Claims, 5 Drawing Sheets

(51) Int. Cl.
*A61B 18/14* (2006.01)
*A61B 18/02* (2006.01)
*A61B 18/24* (2006.01)
*A61N 1/05* (2006.01)
*A61N 1/36* (2006.01)
*A61B 5/0488* (2006.01)
*A61B 5/0492* (2006.01)
*A61B 5/00* (2006.01)
*A61B 18/08* (2006.01)
*A61B 18/20* (2006.01)
*A61B 18/00* (2006.01)
*A61B 17/32* (2006.01)
*A61B 18/06* (2006.01)

(56) References Cited

U.S. PATENT DOCUMENTS

| | | |
|---|---|---|
| 6,351,665 B1 | 2/2002 | Koch |
| 6,795,725 B2 | 9/2004 | Koch |
| 7,160,254 B2 | 1/2007 | Noar |
| 7,468,060 B2 | 12/2008 | Utley et al. |
| 8,055,334 B2 | 11/2011 | Savage |
| 2003/0114770 A1 | 6/2003 | Koch |
| 2005/0096638 A1 | 5/2005 | Starkebaum et al. |
| 2005/0240239 A1 | 10/2005 | Boveja et al. |
| 2006/0015162 A1 | 1/2006 | Edward et al. |

CATHETER STRUCTURE AND METHOD FOR LOCATING TISSUE IN A BODY ORGAN AND SIMULTANEOUSLY DELIVERING THERAPY AND EVALUATING THE THERAPY DELIVERED

FIELD

The invention relates to an endoscopic catheter and, more particularly, to a catheter structure and method for locating the main pathways of electrical generation in an organ of the body, delivery therapy to the located pathways, and for evaluating the therapy delivered.

BACKGROUND

Gastric myoelectrical activity comprises slow waves or pacesetter potentials and, action potential activity. Patients with unexplained dyspepsia symptoms or unexplained nausea and vomiting often have no obvious cause for these symptoms when no peptic ulcer disease, reflux disease or gallbladder abnormalities are found. Gastric dysrhythmias are frequent pathophysiological findings in these patients. Gastric dysrhythmias are termed bradygastrias (1.0-2.5 cpm) and tachygastrias (3.7-10.0 cpm). These gastric dysrhythmias have been defined in many different patient groups where dyspepsia symptoms are present.

U.S. Pat. No. 6,795,725 B2 discloses a catheter structure that can be placed into a human organ, such as the stomach, under direct vision via an endoscope to record myoelectric activity of the organ. These recordings indicate the presence of normal 3-cpm activity at baseline and in other activity in response to a variety of foods or drugs. Although the catheter structure is effective in locating the source of gastric myoelectrical activity, the catheter structure is limited in providing treatment or therapy at the source of the myoelectrical activity.

Accordingly, there is a need to provide catheter structure that can not only locate the main pathways of electrical generation in a human organ, but can simultaneously delivery a variety of therapies and evaluate the effectiveness of the therapy at the tissue having the located pathways.

SUMMARY

An object of the invention is to fulfill the need referred to above. In accordance with the principles of the present invention, this objective is achieved by providing a catheter structure for use with an electroviscerogram (EVG) system. The catheter structure includes an elongated tube structure having distal and proximal ends. Three electrodes are associated with distal end of the tube structure and are constructed and arranged to obtain signals relating to myoelectrical activity internally of an intra-abdominal organ to thereby locate targeted tissue that includes main pathways of electrical generation in the organ. Therapy delivery structure, associated with the distal end of the tube structure and separate from the electrodes, is constructed and arranged to provide therapy at the targeted tissue simultaneously as the electrodes obtain the signals at the targeted tissue so that effectiveness of the therapy can be monitored.

In accordance with another aspect of the invention, a method provides therapy to an intra-abdominal body organ of a patient. The method provides catheter structure including electrodes and therapy delivery structure, separate from the electrodes. The catheter structure is inserted into an internal cavity of the organ endoscopically. A baseline electroviscerogram (EVG) rhythm of the organ is determined by using the electrodes. Signals are obtained with the electrodes that relate to myoelectrical activity of the organ to thereby locate targeted tissue that includes main pathways of electrical generation in the organ. Therapy is provided with the therapy delivery structure at the targeted tissue simultaneously as the electrodes obtain the signals at the targeted tissue. The signals are evaluated to determine the effectiveness of the therapy provided. The results of the therapy provided are compared to the baseline EVG rhythm.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings, wherein like reference numerals refer to like parts, in which.

DETAILED DESCRIPTION OF EXEMPLARY EMBODIMENTS

Figure 1:
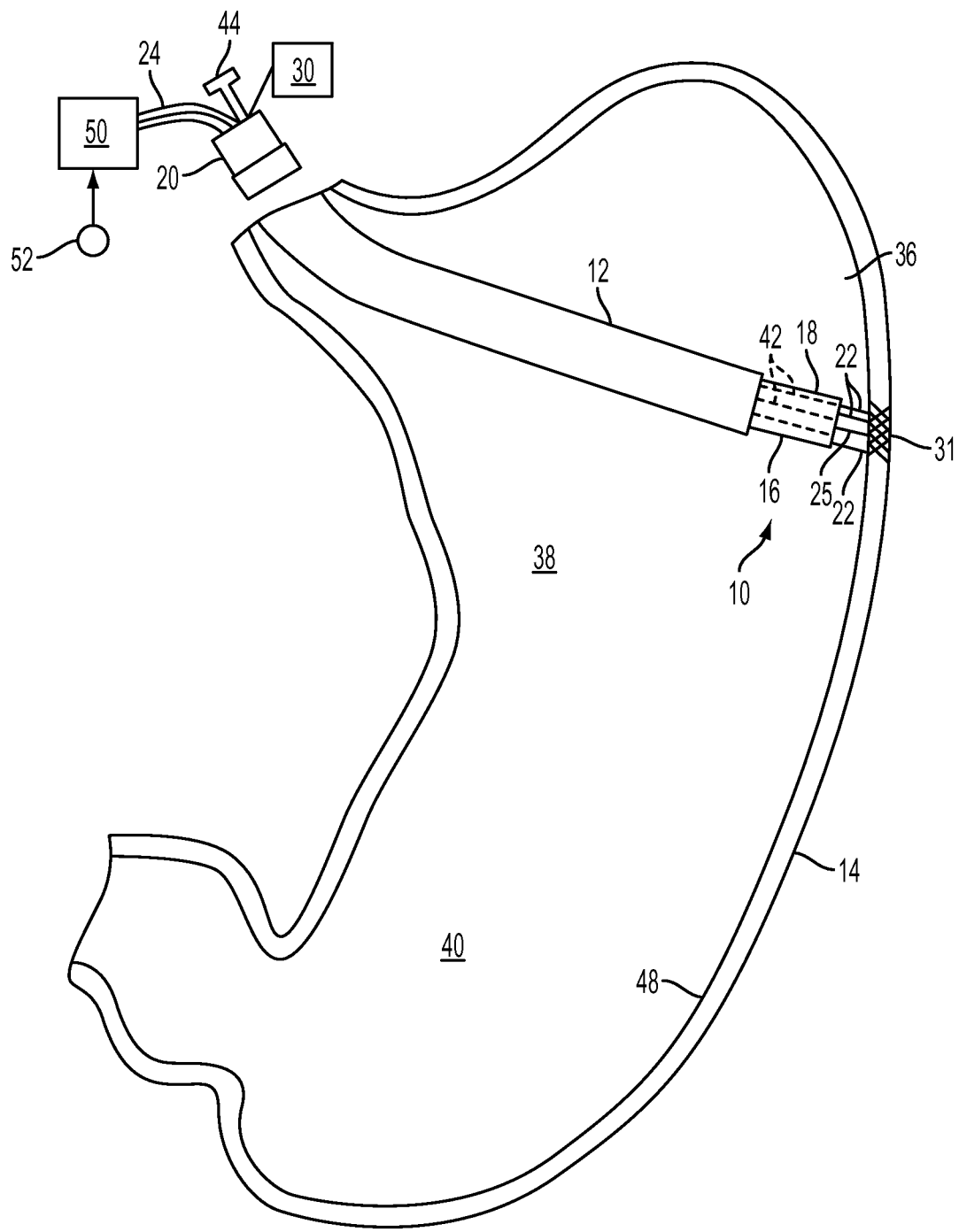
FIG. 1 is perspective view of a catheter structure, provided in accordance with the principles of the invention, shown inserted into a stomach with electrodes and therapy delivery structure thereof engaged with targeted tissue of the stomach.
Figure 2:
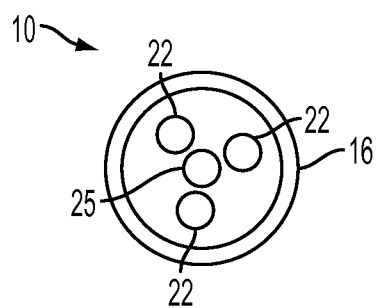
FIG. 2 is an enlarged distal end view of the catheter structure of FIG. 1.

With reference to FIG. 1, a catheter structure, provided in accordance with the invention, is shown generally indicated at 10 inserted via an endoscope 12 into a human organ, such as a stomach 14. The catheter structure 10 includes an elongated tube structure 16 having a distal end 18 and a proximal end 20. Three electrodes 22 are associated with the distal end 18 of the tube structure 16 so as to preferably be moved from a substantially retracted position with respect to distal end 18 of the tube structure 16 to an operative position extending directly from the distal end 18. A signal wire 24 is associated with each electrode 22 for obtaining signals from the electrodes as will be explained more fully below. The wires 24 extend within the tube structure 16 to the proximal end 20 thereof. An end view of the catheter structure 10 is shown in FIG. 2.

Figure 3:
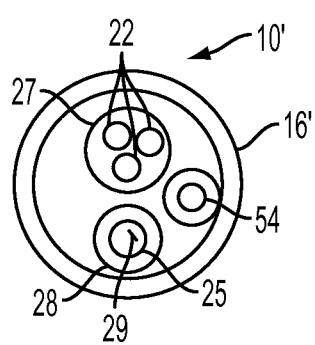
FIG. 3 is an enlarged distal end view of a second embodiment of the catheter structure having separate lumens for the electrodes and therapy delivery structure.

Therapy delivery structure 25, separate from the electrodes 22, is also provided in the tube structure 16 of the catheter structure 10. In the embodiment of FIGS. 1 and 2, the therapy delivery structure 25 is provided generally centrally in the tube structure 16 along with the electrodes 22. However, the therapy delivery structure 25 can be provided in any orientation with respect to the electrodes 22 and thus need not be centrally located. Alternatively, with reference to FIG. 3, a within the tube structure 16' of the catheter 10', a first lumen 27 can contain all of the electrodes 22 and a second, separate lumen 28 can contain the therapy delivery structure 25.

To provide a negative impact on the physiology of the human organ 14 such as, for example, providing a therapeutic impact by producing negative effects on the normal physiological function of the organ, the therapy delivery structure 25 is a device connected with a source of energy 30 to deliver the energy to targeted tissue 31 of the human organ 14. In particular, the therapy delivery structure 25 can be 1) a radio frequency ablation device such as an needle 29 for delivering radio frequency energy to ablate tissue of the organ 14; 2) a microwave ablation device for delivering microwave energy to ablate tissue of the organ 14; 3) an ultrasonic ablation device for delivering ultrasonic wave energy to ablate tissue of the organ 14; 4) a cryoablation device for delivering cryogenic energy to freeze and kill the tissue of the organ 14; and 5) a laser ablation device for delivering laser energy to ablate tissue of the organ 14, all of which are disclosed in U.S. Patent Application Publication No. 2005/0240239A1, the contents of which is hereby incorporated by reference into this specification. It can be appreciated that the therapy delivery structure 25 can be any device capable of altering tissue of a human organ by using, besides those mentioned above, chemical energy or agents, thermal energy, mechanical sources, bipolar, multipolar or impedance controlled radio frequency electrical energy, or other sources of energy. As used herein, "ablate" can include any means of altering tissue such as, for example, cutting, destroying, burning, killing, etc. to provide a negative therapeutic impact on the physiology of the organ 14. For example, the therapy delivery structure can include a tissue harvesting device such as a biopsy needle or forceps or scalpel to remove or cut tissue from the organ.

Figure 4:
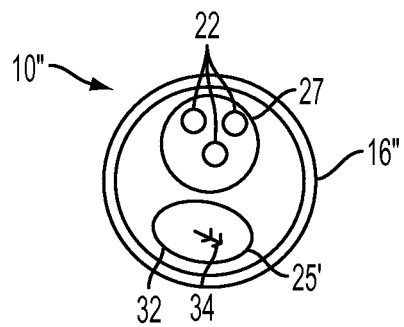
FIG. 4 is an enlarged distal end view of a third embodiment of the catheter structure, showing an implant as the therapy delivery structure.

Instead of negatively impacting the physiology of the human organ 14, there are times when one wants to provide a positive impact. In these situations, instead of ablating tissue, tissue is electrically or chemically stimulated or the tissue is marked for later treatment. For example, to electrically stimulate tissue, the source of energy 30 is preferably electrical energy and the therapy delivery structure 25 preferably includes an electrode 33 (FIG. 6) to engage and provide electrical stimulation to targeted tissue of the human organ 14. Alternatively, for a more permanent solution, with reference to FIG. 4, the therapy delivery structure 25' can include an electrical stimulation device as an implant 32 provided in the tube structure 16". The implant 32 can include a barb 34 at an end thereof and can be delivered through the catheter 10' so as to be implanted and left in targeted tissue 31 of the human organ 14, as explained more fully below. The implant 32 may be delivered by a plunger (not shown) of the therapy delivery structure 25'. Instead of providing electrical stimulation, the implant 32 can provide synthetic materials, cells, tissues/bioengineered tissues and/or chemicals.

Figure 5:
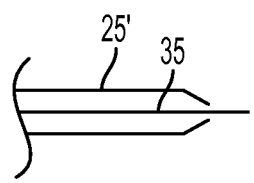
FIG. 5 is a partial view of another embodiment of the therapy delivery structure in the form of a needle.

To mark the targeted tissue 31, as shown in FIG. 5, the therapy delivery structure 25" may include a needle that delivers, for example, India ink 35, or may be a device that can heat and gently burn portions of the targeted tissue 31 or tissue nearby. Since the embodiment of FIG. 5 shows a separate lumen 28 for the therapy delivery structure 25, the needle for the ink 35 can be provided in the lumen 28 to mark the tissue. The needle can thereafter be removed from the lumen 28 and then another therapy delivery structure such as the electrode 33 or an ablating device can be inserted into the lumen 28 to provide treatment or therapy to the marked tissue.

When being inserted into the human organ 14, the electrodes 22 and therapy delivery structure 25 are in an insertion position. More particularly, the electrodes 22 and therapy delivery structure 25 are retracted, disposed near the distal end 18 of the tube structure 16. In the illustrated embodiment, the electrodes 22 are delivered into the lumen 36 of the stomach body 38 and/or antrum 40 in order to record myoelectrical activity from the stomach (or other hollow organ) 14 within the abdominal cavity.

The electrodes 22 and therapy delivery structure 25 are delivered via the tube structure 16 that is passed through the biopsy channel of a standard endoscope 12. In the illustrated embodiment, three electrodes 22 are provided, one for a positive signal, one for a negative signal and one for ground. Each electrode 22 is a recording electrode and is preferably of the type disclosed in U.S. Pat. No. 6,795,725 B2, the content of which is hereby incorporated by reference into this specification.

Figure 6:
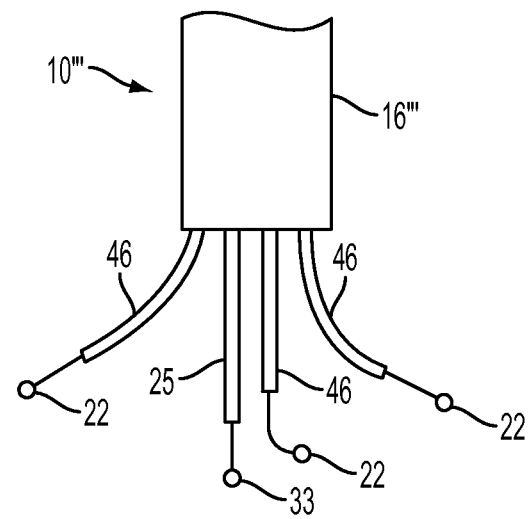
FIG. 6 is an enlarged side view of a distal end of a catheter structure provided in accordance with a fourth embodiment.

In one embodiment, to move the electrodes 22 and the therapy delivery structure 25 between the retracted and extended positions, actuating structure 42, 44 is provided. In the embodiment, the actuating structure can be, for example, one or more wires 42 operatively associated with the electrodes 22 that are manually movable separately, or in unison at the proximal end of the tube structure 16. For example, FIG. 1 shows a single plunger 44 coupled to the wires 42. Movement of the plunger 44 extends and retracts the electrodes 22 in unison. Alternately, instead of retracting and relocating the electrodes 22 to search for the targeted tissue 31, with reference to FIG. 6, the catheter 10''' can include a plurality of lumens 46 within the tube structure 16. Each lumen 46 contains a different electrode 22 so that each electrode 22 can be directed separately in different directions to expand the diagnostic tracking location and allow multi-treatment and sensing sites. In the embodiment of FIG. 6, the electrodes can be retractable for ease of inserting/removing the catheter 10" to/from the human organ 14.

With reference to FIG. 1, when the tube structure 16 is placed within the organ 14 via the endoscope, the electrodes 22 are extended to impinge upon the mucosal lining 48 or pierce the mucosa to a depth of preferably 2-4 mm. In the extended position, the electrodes are spaced apart between about 1-10 mm and are arranged substantially on a common curvilinear surface. In this way gastric myoelectrical activity from the interstial cells of Cajal and/or smooth muscle and/or enteric neurons are recorded from the three electrodes 22. The output of each electrode 22 is a raw signal. In particular, the raw signal is a bioelectrical signal recorded from the lining 48 that reflects the myoelectrical activity of the stomach. The outputs of the electrodes 22 are sent to an electroviscerogram (EVG) system 50 preferably of the type disclosed in U.S. Pat. No. 7,124,654, the content of which is hereby incorporated by reference into this specification.

Respiration rate from the patient is also detected via sensor 52 placed on the chest of the patient. The respiration signal from sensor 52 is used by the system 50 to monitor artifact caused by respiration movements and/or body movements of the patient. The electrical recordings at each site within the organ 14 continue for at least 2 minutes but may continue as long as feasible. Signals from the electrodes 22 received by the system 50 are used to locate main pathways of electrical generation in a human organ 14 (in the stomach, for example, the pacemaker region) to locate the targeted tissue 31. The electrodes 22 may need to be moved around the human organ 14 to find these pathways of electrical generation. Data from the system 50 can be used by a physician to analyze the signals and perform clinically relevant analyses for interpretation to study myoelectric activity, as disclosed in U.S. Pat. No. 7,124,654.

As noted above, the electrodes 22 are used to locate the targeted tissue 31 for treatment. However, to provide for more precise locating of the tissue to be treated, with reference to FIG. 3, the catheter 10' can include a bio-probe or sensor 54. The sensor 54 is constructed and arranged to detect hormone concentrations or cell-specific chemicals to locate the most optimum level in the targeted tissue 31 for treatment.

Figure 7:
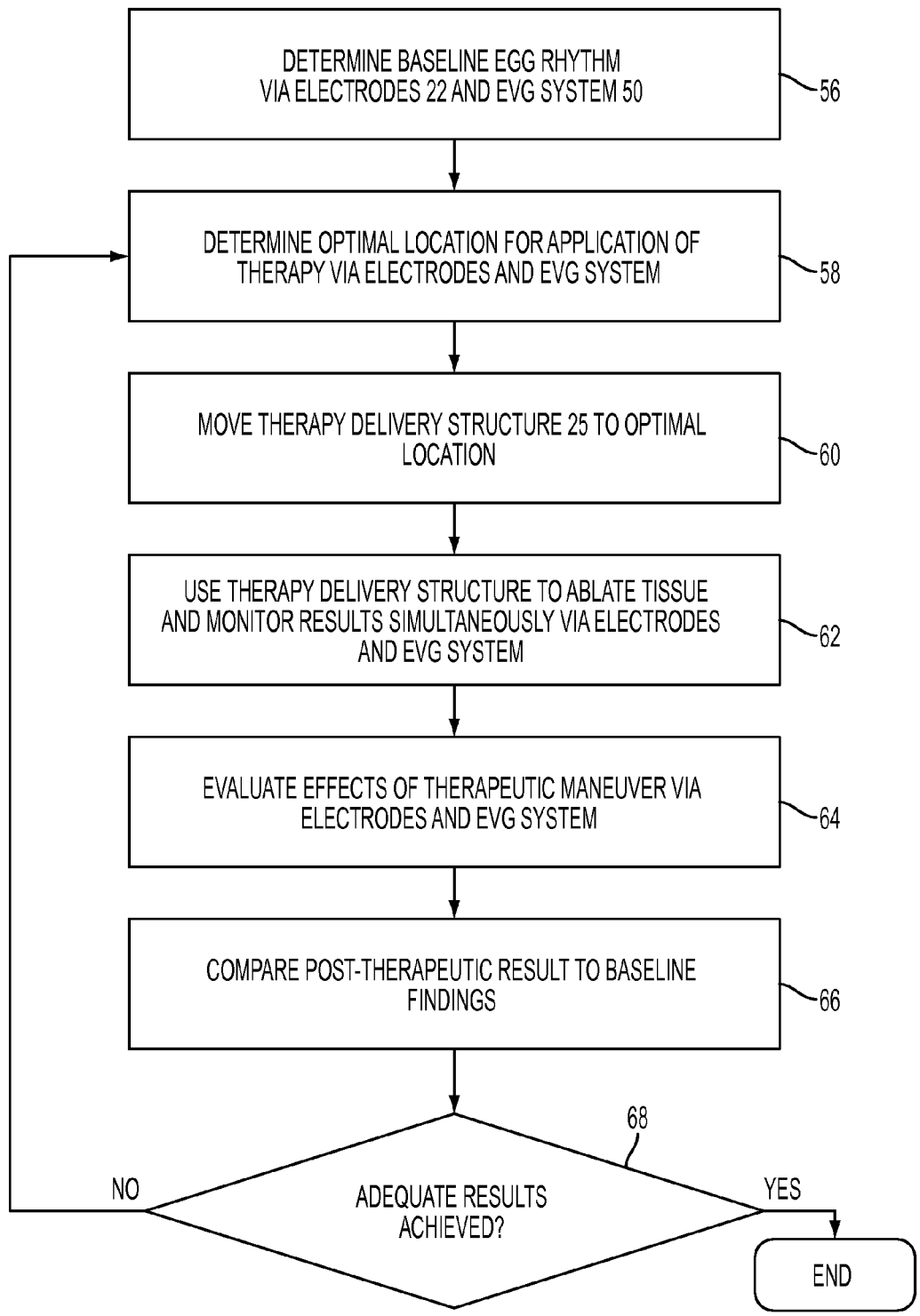
FIG. 7 is a flow chart showing steps for using the catheter structure to determine an optimal location of tissue to be ablated while simultaneously monitoring to evaluate the effects of the ablation.

With reference to FIG. 7, a method of ablating targeted tissue in a human organ is shown. In step 56, when the catheter structure 10 is inserted into the stomach 14, a baseline electroviscerogram (EVG) or EGG rhythm is determined by the EVG system 50 using signals from the electrodes 22 engaged with the lining 48. In step 58, the optimal location (targeted tissue 31) is determined for the application of therapy using the electrodes 22 and EVG system 50. The therapy delivery structure 25 is moved to the optimal location in step 60. In step 62, the therapy delivery structure 25 is used to ablate at least portions of the targeted tissue 31 at the optimal location and the results of the ablation are monitored simultaneously via the electrodes 22 (still in place at the optimal location) and the EVG system 50. The ablation provides a negative impact on the physiology of the human organ or stomach 14. In step 64, the effects of the therapeutic maneuver (ablation) are evaluated via the electrodes 22 and EVG system 50. In step 66, the post-therapeutic results are compared to the baseline finding of step 56 via a processor of the EVG system 50. In step 68, if adequate results are achieved, the method is ended, if not, the method returns to step 58.

Figure 8:
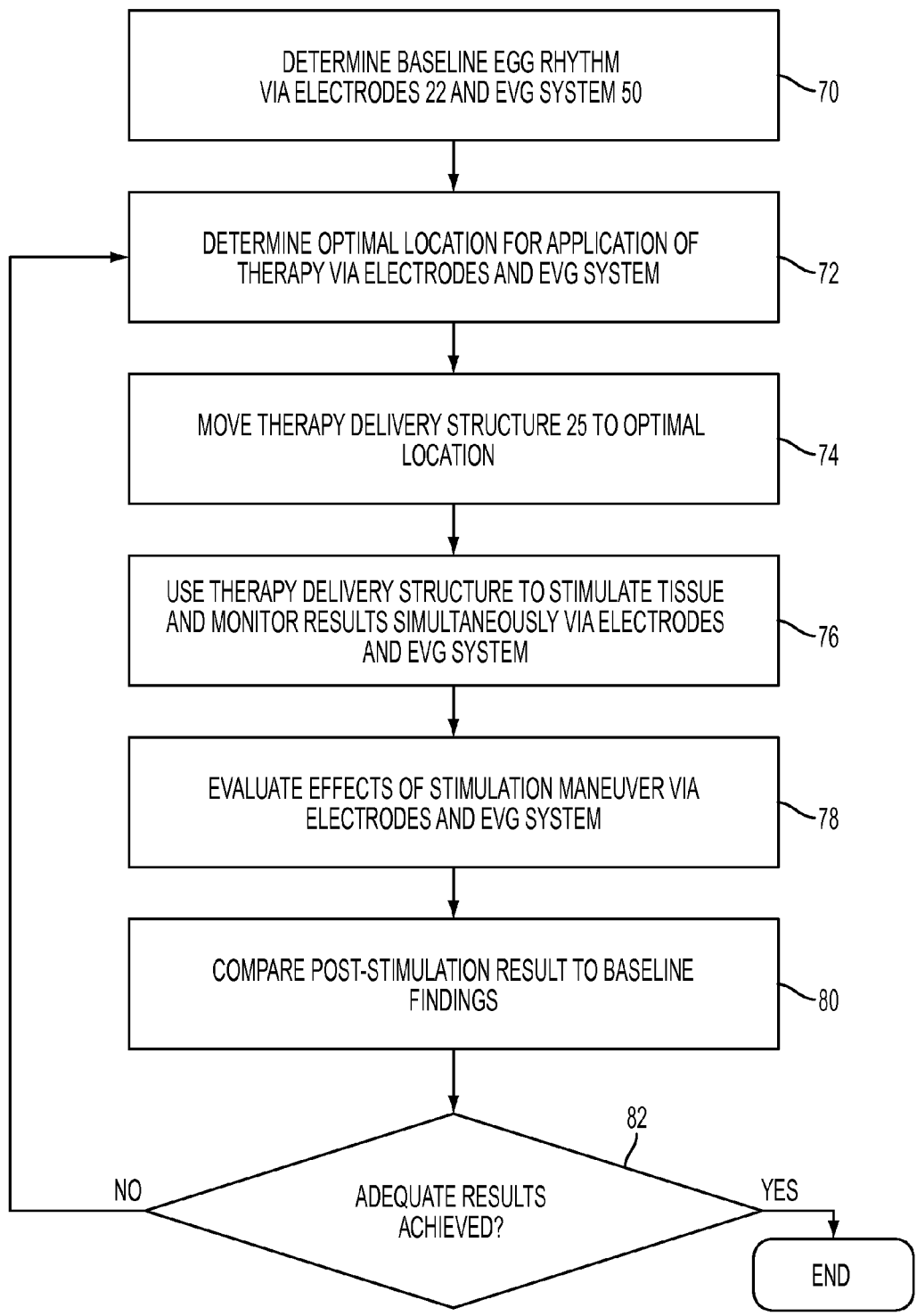
FIG. 8 is a flow chart showing steps for using the catheter structure to determine an optimal location of tissue to be stimulated while simultaneously monitoring to evaluate the effects of the stimulation.

With reference to FIG. 8, a method of stimulating targeted tissue in a human organ is shown. In step 70, when the catheter structure 10 is inserted into the stomach 14, a baseline electroviscerogram (EVG) or EGG rhythm is determined by the EVG system 50 using signals from the electrodes 22 engaged with the lining 48. In step 72, the optimal location (targeted tissue 31) is determined for the application of therapy using the electrodes 22 and EVG system 50. The therapy delivery structure 25 is moved to the optimal location in step 74. In step 76, the therapy delivery structure 25 is used to electrically stimulate at least portions of the targeted tissue 31 at the optimal location and the results of the stimulation are monitored simultaneously via the electrodes 22 (still in place at the optimal location) and the EVG system 50. Step 76 can include using the electrode 33 of FIG. 5 to stimulate tissue or can include placing the implant 32 of FIG. 4 into the tissue to stimulate the tissue. The electrical stimulation provides a positive impact on the physiology of the human organ or stomach 14. In step 78, the effects of the stimulation are evaluated via the electrodes 22 and EVG system 50. In step 78, the post-stimulation results are compared to the baseline finding of step 70 via a processor of the EVG system 50. In step 80, if adequate results are achieved, the method is ended, if not, the method returns to step 72 if using the electrode 33. If using the implant 32, the implant is removed from the tissue and then the method returns to step 72 to determine the better location to place the implant 32.

Figure 9:
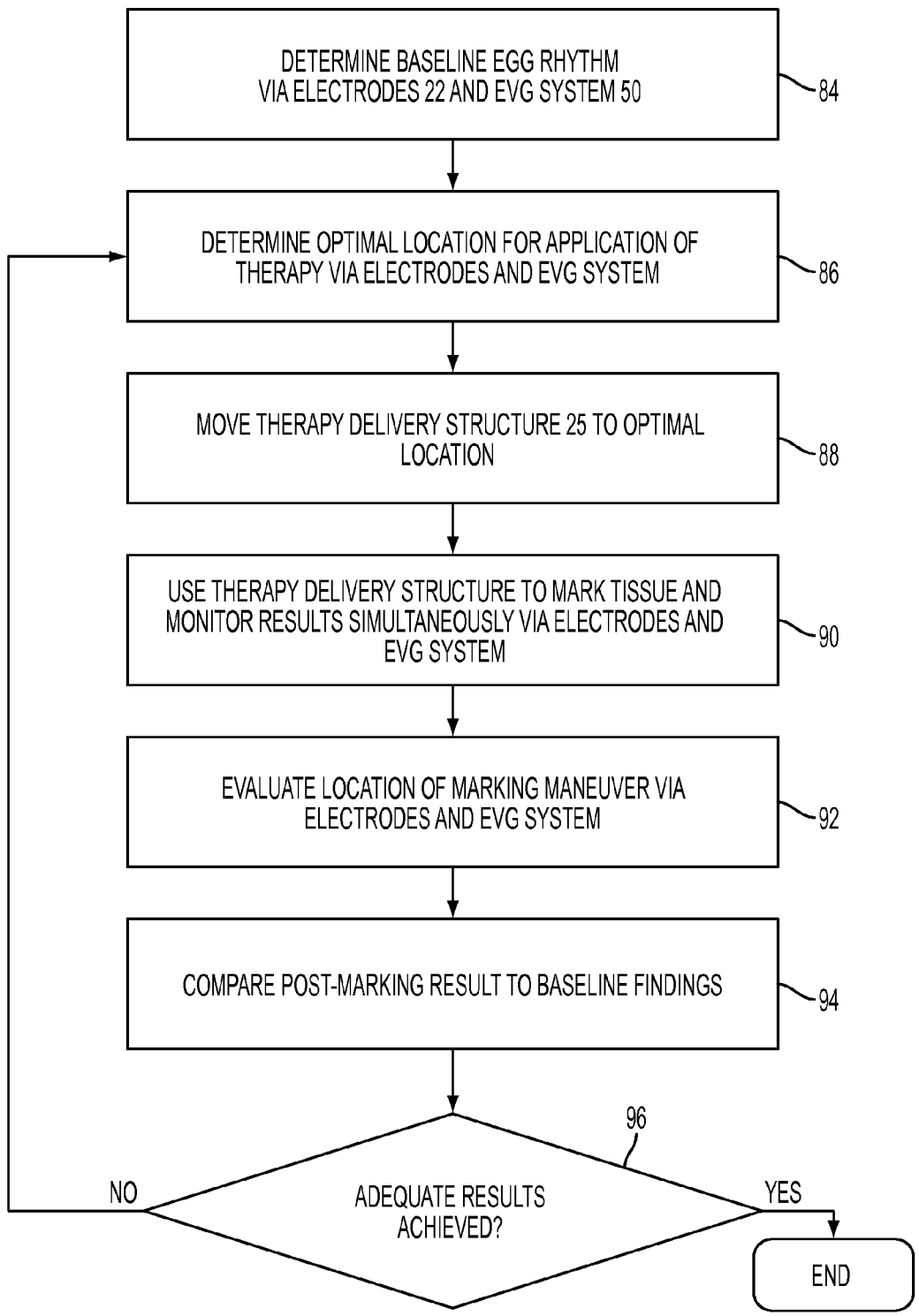
FIG. 9 is a flow chart showing steps for using the catheter structure to determine an optimal location of tissue to be treated, marking the tissue and simultaneously monitoring to evaluate the effects of the marking.

With reference to FIG. 9, a method of marking targeted tissue in a human organ for later treatment is shown. In step 84, when the catheter structure 10 is inserted into the stomach 14, a baseline electroviscerogram (EVG) or EGG rhythm is determined by the EVG system 50 using signals from the electrodes 22 engaged with the lining 48. In step 86, the optimal location (targeted tissue 31) is determined for the application of therapy using the electrodes 22 and EVG system 50. The therapy delivery structure 25 is moved to the optimal location in step 88. In step 90, the therapy delivery structure 25 is used to mark at least portions of the targeted tissue 31 at or near the optimal location and the results of the marking are monitored simultaneously via the electrodes 22 (still in place at the optimal location) and the EVG system 50. In step 92, the effects of the marking are evaluated via the electrodes 22 and EVG system 50. In step 94, the post-marking results are compared to the baseline finding of step 84 via a processor of the EVG system 50. In step 96, if adequate results are achieved, the method is ended, if not, the method returns to step 86.

With the catheter structure of the embodiments:

1. The optimal location or source of the myoelectrical activity can be determined by the EVG system 50 because the electrodes 22 are placed inside the organ under direct vision via the endoscope 12;

2. The frequency and amplitude of the myoelectrical activity are directly measured without interference from abdominal musculature, adipose tissue or skin;

3. The electrical patterns in the organ can be mapped in order to determine normal electrical pathways;

4. The electrical patterns in the organ regarding various diseases or disorders can be mapped and extent of damage to the electrical network in these diseases and disorders can be determined;

5. The therapy delivery structure 25 simultaneously, with the electrode 22 monitoring, ablates, stimulates or marks the tissue at the optimal location;

6. The electrodes 22 and EVG system 50 permits evaluation of the ablation, stimulation or marking since the electrodes remain in the tissue at the optimal location during the ablation, simulation or marking procedure;

7. Electrical activity of the stomach can be altered to limit appetite or to stimulate appetite; and 8. Since the patient will be sedated and myoelectrical activity is monitored at the organ's lining, artifact caused by respiration can be taken into account by using the respiration sensor 52.

Although the catheter structure was shown for use inside the stomach it can be appreciated that the catheter structure can be modified by changing the length thereof when designed for use in the following other organs such as, for example, Duodenum and jejunum; Bile duct; Rectum and sigmoid colon, terminal ileum, ascending and transverse colon; Urinary bladder; Uterus and oviducts.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A method of providing therapy to an intra-abdominal body organ of a patient, the method comprising the steps of:
   a) providing catheter structure including three electrodes and therapy delivery structure; wherein the therapy structure is separate from, different from, and not connected with the three electrodes,
   b) inserting the catheter structure into an internal cavity of the organ endoscopically,
   c) determining a baseline electroviscerogram (EVG) rhythm of the organ using the three electrodes,
   d) obtaining signals with the three electrodes that relate to myoelectrical activity of the organ to thereby locate targeted tissue that includes main pathways of electrical generation in the organ,
   e) providing therapy, with the therapy delivery structure, at the targeted tissue simultaneously as the three electrodes obtain the signals at the targeted tissue,
   f) evaluating the signals to determine the effectiveness of the therapy provided, and
   g) comparing results of the therapy provided to the baseline EVG rhythm.

2. The method of claim 1, wherein after the comparing step, if the resulting therapy provided is not adequate, the method includes repeating steps d) through g).

3. The method of claim 1, wherein the step of providing therapy includes ablating at least portions of the targeted tissue.

4. The method of claim 1, wherein the step of providing therapy includes stimulating at least portions of the targeted tissue.

5. The method of claim 1, wherein the step of providing therapy includes implanting in a portion of the targeted tissue, an electrical stimulation device to stimulate the targeted tissue.

6. The method of claim 1, further comprising using a sensor to detect hormone concentration or cell specific chemicals in the targeted tissue to identify specific tissue of the targeted tissue to receive the therapy.

7. The method of claim 1, further comprising:
   providing a respiration sensor to monitor respiration of the patient, and
   using an electroviscerogram (EVG) system to receive a signal from the respiration sensor to determine artifact and to receive the signals from the electrodes so that the EVG system performs the comparing and evaluating steps.

* * * * *